United States Patent [19]

Mikhail

[11] Patent Number: 4,606,649
[45] Date of Patent: Aug. 19, 1986

[54] ASSEMBLY FOR CONCURRENT THERMOGRAVIMETRY AND DIFFERENTIAL THERMAL ANALYSIS

[75] Inventor: Shaheer A. Mikhail, Nepean, Canada

[73] Assignee: Her Majesty the Queen in right of Canada, as represented by the Minister of Energy, Mines and Resources, Ottawa, Canada

[21] Appl. No.: 690,946

[22] Filed: Jan. 14, 1985

[51] Int. Cl.$^4$ ............................................. G01N 25/00
[52] U.S. Cl. ..................................... 374/10; 374/12; 374/14
[58] Field of Search ....................... 374/10, 11, 12, 13, 374/14; 422/51, 78

[56] References Cited

U.S. PATENT DOCUMENTS

| 3,045,472 | 7/1962 | Paulik et al. | 374/10 |
| 3,271,996 | 9/1966 | Paulik et al. | 374/10 |
| 3,303,689 | 2/1967 | Paulik et al. | 374/12 |
| 3,491,581 | 1/1970 | Roberts et al. | 374/12 |
| 3,519,547 | 7/1970 | Paulik et al. | 204/405 |
| 3,858,433 | 1/1975 | Nearhoof | 374/10 |
| 4,031,740 | 6/1977 | Achermann | 374/11 |
| 4,095,453 | 6/1978 | Woo | 374/13 |

FOREIGN PATENT DOCUMENTS 1324982  7/1973  United Kingdom ................. 374/10

OTHER PUBLICATIONS

Oura et al, "Simultaneous DTA-TG Thermal Analyzer" Shamadzu Rev. (Japan), vol. 32, No. 1, 1975, pp. 119-125.
Netzsch Pamphlet entitled "Simultaneous Thermal Analysis" issued by Netzsch-Geratebau GmbH D-8672 Selb of Germany.
Pamphlet entitled "STA Simultaneous Thermal Analysis System" issued by Stanton Redcroft Ltd. of England.
Paper by Jen Chiu entitled "Technique for Simultaneous Thermogravimetric, Derivative Thermogravimetric, Differential Thermal, and Electrothermal Analyses".
Paper entitled "Recent Instrumental Developments" by W. W. Wendlandt, National Bureau of Standards Special Publication 580, Proceedings of the Work-Shop on the State-of-the-Art of Thermal Analysis held at NBS, Gaithersburg MD. May 21-22, 1979 (issued May 1980).
Operator's Manual of the DuPont 951 TGA Instrument entitled "951 TGA Thermogravimetric Analyzer" issued by the DuPont Co. Sep. 1983.
A brochure on the DuPont 1090 Therman Analysis System issued by the DuPont Co.

Primary Examiner—Charles E. Frankfort
Assistant Examiner—Thomas B. Will

[57] ABSTRACT

A modification to thermogravimetric analyzers with data acquisition devised to allow concurrent TG (thermogravimetry) and DTA (differential thermal analysis) measurements employs three samples mounted close to each other in a TG furnace. Two of the samples are active ones, i.e. of the material to be analyzed, and the third is a reference sample of an inert material. The first active sample is suspended from the beam of a thermobalance. The change in weight of this sample is recorded and plotted versus the temperature of the second active sample. The sample thermocouple and another identical thermocouple are placed in contact with crucibles containing the second active sample and the reference material, respectively. The differential temperature between the sample and the reference material is taken from the two identical thermocouples. The differential signal is amplified and plotted against the temperature of the second active sample. The two active samples are substantially identical to each other in geometry, i.e. amount and shape.

2 Claims, 1 Drawing Figure

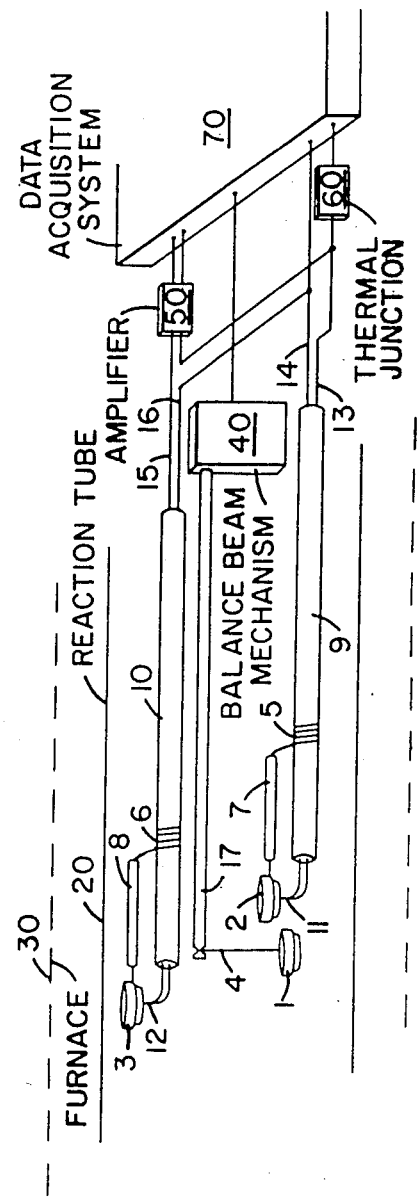

ASSEMBLY FOR CONCURRENT THERMOGRAVIMETRY AND DIFFERENTIAL THERMAL ANALYSIS

BACKGROUND OF THE INVENTION

This invention relates to a thermal analysis system for concurrent thermogravimetry and differential thermal analysis.

Thermogravimetry (hereinafter referred to as TG) is a procedure whereby a sample of a substance to be analysed is subjected to a controlled temperature program. Changes in the mass (weight) of the sample are detected and plotted against a steady temperature rise (dynamic TG) and also, if desired, against time (at constant temperature, isothermal TG).

Differential thermal analysis (hereinafter referred to as DTA), on the other hand, is essentially a qualitative method of comparing thermal changes in a sample of the substance under study with those in a sample of an inert reference substance, e.g. alumina. The two samples are subjected to the same temperature program, while the actual temperatures of the samples are measured by fine thermocouples. Differential connection of the thermocouples provides an output signal representative of any exothermic or endothermic change taking place in the active sample. This value is also plotted against temperature and, if desired, time. Another variable that can be introduced is the nature of the ambient atmosphere. For example, different plots will be obtained for DTA carried out in air or in an inert atmosphere such as argon.

Together, DTA and TG constitute a powerful combination to provide valuable information about the thermal behaviour of materials under various conditions and for the identification of substances.

PRIOR ART

Correlation of the results of the two techniques has, however, always been questionable to some extent, due to unavoidable differences in experimental conditions. Ideally, both techniques should be applied to the same sample at the same time, so-called simultaneous thermal analysis. See, for example U.S. Pat. No. 3,045,472 issued July 24, 1962 to F. Paulik et al. The basic problem with simultaneous TG-DTA is that it is impossible to measure the temperature of the active sample without to some degree interfering with the measurement of its weight. In an endeavor to minimise this problem, extremely fine wires have been taken from the thermocouples, the wire from the active sample leaving the system as close as possible to the fulcrum of the balance beam. Even so, the weight measurement is so delicate that total avoidance of interference with the weight measurement is difficult. In practice, only a few thermal analysis systems designed to perform simultaneous measurements are actually available on the market and they are relatively expensive due to the complexity of construction necessary to minimise the interference problem sufficiently to achieve sensitivities comparable to those attainable with individual measurements. Such an instrument, STA429*, is marketed by Netzsch-Gerätebau GmbH of Selb, Germany and, as STA780*, by Stanton Redcroft Ltd., of London, England.
* Trade Mark A viable and simple alternative to simultaneous thermal analysis is concurrent thermal analysis in which DTA and TG are conducted, at the same time, but on two separate active samples placed close to each other inside the reaction tube in the furnace. Although the measurements are done on two individual samples, correlation of the results is more acceptable, since both samples (with the same geometry) are subjected to the same thermal program and are exposed to the same conditions in the furnace, but without need for a thermocouple to be in contact with the sample being weighed. A description of a concurrent thermal analysis technique is contained in a paper by J. Chiu published in Anal. Chem. 39(1967) pages 861-867. Mr. Chiu entitled his paper "Technique for Simultaneous Thermogravimetric, Derivative Thermogravimetric, Differential Thermal, and Electrothermal Analyses." Although he used the term "simultaneous," the technique Chiu described employs two rather than one active sample of the material under study. See, for example, Chiu's FIG. 3 which shows a quartz balance beam supporting a first sample for the TG measurement, flanked by a pair of quartz tubes respectively containing a second active sample and a reference sample, together with thermocouples for the DTA measurement.

Another discussion of concurrent TG - DTA measurements is contained in W. W. Wendlandt "Recent Instrument Developments" published as the Proceedings of the Workshop on the State-of-the-Art of Thermal Analysis held at NBS, Gaithersburg, MD, May 21-22, 1979: National Bureau of Standards Special Publication 580, 1980, pp 219-233.

SUMMARY OF THE INVENTION

The present invention relates to improvements in concurrent TG-DTA.

More specifically, the invention consists of an assembly for concurrent TG-DTA measurements comprising (a) a furnace for providing a controlled temperature program; (b) three containers for respectively supporting a first active sample of a material to be analysed, a second active sample of said material and a third reference sample of an inert material, said first and second samples being substantially identical to each other in amount and shape; (c) a balance beam for weighing the first container supporting said first sample while located in the furnace and providing a first output signal representative of said weight; (d) means mounting the second and third containers supporting said second and third samples in the furnace in the vicinity of the first sample; (e) a pair of thermocouples in contact with respective ones of said second and third containers; (f) circuit means for providing a second output signal representative of the difference in temperature of said second and third samples and for providing a third output signal representative of the temperature of the second sample; and (g) a data acquisition system connected to receive said output signals for plotting the first and third output signals against each other to provide a TG measurement and for plotting the second and third output signals against each other to provide a DTA measurement. The second signal is normally amplified to the level of detection of the data acquisition system, e.g. recorder, by using a d.c. amplifier.

BRIEF DESCRIPTION OF THE DRAWINGS

The accompanying drawing is a perspective view of a preferred embodiment of the present invention.

DETAILED DESCRIPTION OF THE PREFERRED EMBODIMENT

It is not believed necessary at this stage of the development of the art to illustrate or describe in detail the manner in which the weight of the active sample is determined for the TG measurement. Suffice to say that in many practical respects, the present invention can be viewed as a modification to the Du Pont 951* TGA thermobalance made by Du Pont Company of Wilmington Delaware to render it capable of concurrent TG-DTA operation, while adopting its basic balance beam structure and circuitry. Du Pont company also markets DTA equipment separately from their TG equipment. This calls for the TG and DTA measurements to be carried out in separate furnaces, in contrast to the concurrent technique with which the present invention is concerned where the same furnace is used to heat the two active samples and one reference sample simultaneously. The present invention, in its theoretical aspects, may also be seen as a modification of the Chiu disclosure discussed above.

*Trade Mark

In the accompanying drawing there is shown a platinum crucible 1 for holding a first active sample suspended by a platinum wire 4 from the end of a quartz balance beam 17. A pair of fixed thermocouple sheaths 9 and 10 support platinum crucibles 2 and 3 for respectively holding a second active sample and a reference sample. These latter crucibles are mounted in ring-like ends of relatively heavy gauge platinum wires 5, 6 that are shielded by ceramic sheaths 7, 8 for most of their lengths and are wound at their other ends around the thermocouple sheaths 9, 10. A pair of identical chromel-alumel thermocouples 11 and 12 are used. The crucibles 2, 3 are made with indentations in their bottom surfaces and rest on the beads of the respective thermocouples. This direct contact between the thermocouples and the crucibles provides a more accurate measurement of sample and reference temperatures in the TG measurement than when the thermocouple is located close to but not in contact with the TG crucible. The latter is the conventional technique used to avoid interference with the sample being weighed.

The assembly shown in the drawing will be located in a reaction tube 20 inside a conventional furnace 30 by which controlled heating rates can be obtained. It will be noted that the complete measuring assembly enters the furnace 30 from one end. This avoids the need to modify the end wall of the reaction tube 20, a principal difference from the design adopted by Wendlandt in the publication mentioned above.

The chromel wires 14, 16 of the two thermocouples are connected together and a differential signal is taken out across the two alumel wires 13, 15, to be amplified using a low noise d.c. amplifier 50 and connected to a data acquisition system 70. This signal provides the basic data required for the DTA measurement. In addition, the two wires 13, 14 from the thermocouple 11 provide the output signal that indicates the temperature of the second active sample (the alumel wire 13 of thermocouple 11 may be connected to the data acquisition system across an electronic ice point or a thermal junction 60 for ambient temperature compensation). This signal defines the temperature that is to be plotted against the differential temperature in the DTA measurement and against the weight in the TG measurement. The signal from a balance beam mechanism 40 represents the weight of the first active sample.

The Du Pont Company also markets a 1090* Thermal Analysis System that provides a microprocessor unit including a digital temperature programmer, plotter, visual display, disk memory and data analyser. Connection of the assembly shown in the accompanying drawing to such a unit will enable the TG and DTA measurements to be analysed, stored and displayed simultaneously. Preferably the TG and DTA values will be plotted together on the same sheet, since their abscissas are common, which facilitates comparison and assessment of the information that these combined measurements represent. Specifically, the 1090 unit receives, records and, when desired, displays simultaneously 4 signals, namely time (t), temperature (T), weight (w) and the derivative ($\Delta w/\Delta t$). The latter signal has been provided by an analog circuit built into the TG module, i.e. the 951 TGA system referred to above. With this module hooked up to the 1090 microprocessor, the derivative circuit is unused, since the derivative ($\Delta w/\Delta t$) is automatically calculated by the microprocessor. Hence a port to the 1090 unit becomes available and can be used to introduce the DTA signal, an important practical advantage, because it avoids any need to modify the 1090 unit and any need to modify the 951 system other than as shown in the accompanying drawing, i.e. to add the DTA samples (a second active sample and the reference sample) as well as a second thermocouple and a low-noise d.c. amplifier.

*Trade Mark

To obtain meaningful data using this TG/DTA concurrent technique, it is essential to maintain the same geometry (amount and shape) for the samples. It has been found that using different geometries results in noticeable differences in the obtained results. Hence the three crucibles should be identical and the two sample crucibles should be filled with the same amount of active sample material.

I claim:

1. Assembly for concurrent TG-DTA measurement comprising
   (a) a furnace for providing a controlled temperature program;
   (b) three containers comprising crucibles substantially identical in size and shape to one another for respectively supporting a first active sample of a material to be analysed, a second active sample of said material and a third reference sample of an inert material, said first and second samples being substantially identical to each other in amount and shape;
   (c) a balance beam for weighing a first of said containers supporting said first sample while located in the furnace and providing a first output signal representative of said weight;
   (d) means mounting a second and a third of said containers respectively supporting said second and third samples in the furnace in the vicinity of the first sample;
   (e) a pair of thermocouples in contact with respective ones of said second and third containers;
   (f) circuit means for providing a second output signal representative of the difference in temperature of said second and third samples and for providing a third output signal representative of the temperature of the second sample; and (g) a data acquisition system connected to receive said output signals for plotting the first and third output signals against each other to provide a TG measurement and for plotting the second and third output signals against each other to provide a DTA measurement;

(h) wherein the balance beam, the thermocouples and the three containers are located in a reaction tube of the furnace closely surrounding the three containers, the balance beam and said means mounting the second and third containers all entering the tube from a single end thereof.

2. Assembly according to claim 1, wherein said data acquisition system has an available port for receiving said second output signal in addition to standard ports for receiving the first and third output signals and a time signal.

* * * * *